United States Patent [19]
McGinity et al.

[11] Patent Number: 5,622,993
[45] Date of Patent: Apr. 22, 1997

[54] STICK FORMULATIONS FOR TOPICAL DRUG DELIVERY OF THERAPEUTIC AGENTS AND USES THEREOF

[75] Inventors: James W. McGinity, Austin; Thomas G. Gerding, Georgetown, both of Tex.; Roland Bodmeier, Berlin, Germany

[73] Assignee: Medical Polymers, Austin, Tex.

[21] Appl. No.: 523,084

[22] Filed: Sep. 1, 1995

Related U.S. Application Data

[62] Division of Ser. No. 345,051, Nov. 14, 1994.

[51] Int. Cl.⁶ .................................................. A61K 31/16
[52] U.S. Cl. ........................................ 514/626; 514/817
[58] Field of Search ................................... 514/626, 817

[56] References Cited

U.S. PATENT DOCUMENTS

| | | | |
|---|---|---|---|
| 3,814,095 | 6/1974 | Lubens | 128/260 |
| 4,048,309 | 9/1977 | Chen et al. | 424/238 |
| 4,226,850 | 10/1980 | Packman et al. | 424/47 |
| 4,702,916 | 10/1987 | Geria | 424/400 |
| 4,704,271 | 11/1987 | Hourihan et al. | 424/66 |
| 4,738,956 | 4/1988 | Scott et al. | 514/179 |

OTHER PUBLICATIONS

Hight, B., "Medical Polymers gets distribution pacts," *Austin American–Statesman*, Nov. 4, 1994.
Chang, "Search for the perfect gel," *Cosmetics and Toiletries*, 92:25–26, 1977.
Barker and Meinstein, "Versatile Gelling Agents for Innovative Stick Products," *Soap/Cosmetics/Chemical Specialties*, 44A–44B, 1982.
Barker, "Sodium Stearate–Based Sticks Proposed Structure," *Cosmetics & Toiletries*, 102:71–80, 1987.
Barker, "Solidified sodium stearate–based sticks," *Cosmetics and Toiletries* 92:73–75, 1977.
Schmolka, "Gel Cosmetics," *Cosmetics & Toiletries*, 99:69–75, 1984.
Teng and Scallet, "New carbohydrate–based gelling agents for organic solvents," *Cosmetics and Toiletries*, 92:39–40, 1977.
Teng et al., "New carbonhydrate–based gelling agents for organic solvents," *Cosmetics and Perfumery*, 90:32–43, 1975.
Vaughan and Baker, "Stick makeup," *Cosmetics and Toiletries*, 92:47–53, 1977.
Schmolka, "BWC surfactants in gel cosmetics," *Cosmetics and Toiletries*, 92:77–79, 1977.
Neulinger, "Use of sugar esters in cosmetic sticks," *Cosmetics and Toiletries*, 92:65–66, 1977.
Fox, "Sticks and Gels A Patent and Literature Update," *Cosmetics & Toiletries*, 102:33–53, 1987.
Fukasawa et al., "New Oil–Gelling Agents for Cosmetics," *Cosmetics & Toiletries*, 103:78–80, 1988.
Geria, "Manufacturing and Packaging Technology of OTC and Cosmetic Sticks," *Cosmetics & Toiletries*, 102:65–70, 1987.
Korbar–Smid, "Magnesium, calcium, and zinc stearate gels with liquid paraffin," *Cosmetics and Toiletries*, 93:33–34, 1978.
Proserpio and Mariotti, "Biphasic gels," *Cosmetics and Perfumery*, 90:41–42, 1975.
Fox, "Gels and Sticks Review and Update," *Cosmetics & Toiletries*, 99:19–54, 1984.
Assasy et al., "Stability of hydrogen peroxide in certain pharmaceutical gels," *Cosmetics and Toiletries*, 91:54–56, 1976.
DeRagon and Daley, "Blemish sticks," *Cosmetics and Toiletries*, 92:39–44, 1977.
Bozic et al., "Magnesium, calcium, and zinc stearate gels with liquid paraffin," *Cosmetics & Toiletries*, 95:25–31, 1980.
Carlson, "Veegum in cosmetic gels and sticks," *Cosmetics and Toiletries*, 92:81–86, 1977.
Barker, "Solidified sodium stearate–based sticks," *Cosmetics and Toiletries*, 92:73–75, 1977.
?*Cosmetics & Toiletries*, 102:53–63, 1987.
"Cosmetic sticks: a digest of patents published 1969–1977," *Cosmetics and Toiletries*, 92:54–64, 1977, author unknown.
"Cosmetic Stick Comprising Water–in–Oil Emulsion (British Patent Specification 1442426)," *Cosmetics and Toiletries*, 92:69–71, 1977, author unknown.
"Gels & Sticks Formulary," *Cosmetics & Toiletries*, 102:107–127, 1987.
"Formulary," *Cosmetics & Toiletries*, 99:77–115, 1984.
"Witepsol®" Fatty Bases for Suppositories, HÜls Aktiengesellschaft, Product Literature (Feb. 1994).
GANEX V–216, International Specialty Products, Sales Specifications, (30 Apr. 1993).
GANEX V–216, ISP Technologies Inc., Material Safety Data Sheet, 1–5 (16 Sep. 1994).
GANEX V–220, International Specialty Products, Sales Specifications, (30 Apr. 1993).
GANEX V–220, ISP Technologies Inc., Material Safety Data Sheet, 1–5 (16 Sep. 1994).
"GANEX®" Alkylated Polyvinylpyrrolidone, Specialty Products for Personal Care, Product Literature (1989).

*Primary Examiner*—Alan L. Rotman
*Assistant Examiner*—Evelyn Huang
*Attorney, Agent, or Firm*—Denise L. Mayfield

[57] ABSTRACT

Stick formulations for topical delivery of water soluble and/or water insoluble agents are disclosed. The stick formulations may contain steroids, antibiotics, antifungals, antihistamines anti inflammatories or local anesthetics. The vehicles comprise a combination of waxes and oils and a surfactant in embodiments involving water soluble agents. Methods for preparing the various stick formulations are also disclosed.

17 Claims, 2 Drawing Sheets

5,622,993

STICK FORMULATIONS FOR TOPICAL DRUG DELIVERY OF THERAPEUTIC AGENTS AND USES THEREOF

This is a divisional of co-pending application Ser. No. 08/345,051, filed Nov. 14, 1994.

BACKGROUND OF THE INVENTION

1. Field of the Invention

The present invention relates generally to stick formulations for the delivery of various therapeutic agents, such as anti-inflammatory agents, insect repellants, local anesthetics, antibiotics, and antifungal agents to skin and various mucosal surfaces of the body. Methods for using and making such stick formulations are also provided.

2. Background of the Invention

Agents applied topically to the skin are generally formulated in liquid or semi-solid formulations including creams, lotions, solutions, aerosols and ointments. Creams, lotions and ointments typically fall into one of four general classes: hydrocarbon bases, absorption bases, emulsion bases and water soluble bases and may be adapted to a variety of drugs. Although these types of formulations are widely used, they tend to be inconvenient and wasteful because of the difficulty in delivering a precise amount of such a preparation just to the area to be treated. This is particularly true of aerosols, which are subject to overspray and incidental inhalation of the product, as well as environmental concerns about propellants and disposal of containers. Ointments and creams are often messy and applied to a wider area than necessary because of their liquid or semi-liquid state. All of these products may also leave a wet, greasy or sticky feeling.

Stick products have been used for cosmetic purposes such as antiperspirants, deodorants, lipsticks and the like. Stick formulations have also been described that include analgesics dissolved in a particular ricinoleate vehicle, such as castor oil, prior to mixture in a stick (U.S. Pat. No. 4,048,309). These sticks must contain enough wax to remain solid, without trapping the active ingredient in the wax in a manner that would prevent drug contact with the skin. The method of manufacturing these sticks includes heating the formulation up to 90° C. in order to melt the carnauba wax, which may cause separation of the components or degradation of the drugs.

U.S. Pat. No. 4,702,916, relates to formulations having 10–65% alcohol, 6–10% of an alkali metal salt of a saturated fatty acid gelling agent having from about C8 to about C22 lengths, about 10–30% water, and oleoresin capsicum, capsicum, capsaicin, camphor, allyl isothiocyanate, methyl nicotinate, menthol, and mixtures thereof. A semi-solid delivery system for hydrocortisone is described in U.S. Pat. No. 4,738,956 and incorporates a volatile silicone such as dimethicone or cyclomethycaine along with a fatty alcohol. These formulations are primarily designed for water insoluble agents and would be less efficient for delivery of water soluble products.

Considerations in preparing stick formulations for the delivery of an active ingredient, such as a drug, include the relative water solubility or lipid solubility of the active ingredient and the stability of the agent in the stick. These, and other technical considerations have continued to create problems in providing a stable and concentrated stick preparation. A need continues to exist for improved stick formulations that are convenient to use, non-messy, and formulated to deliver water soluble and/or water insoluble agents topically to the skin with good spreadability and stability.

SUMMARY OF THE INVENTION

The present invention addresses one or more of the problems in the art relating to the formulation of water soluble drug and non-water soluble drug containing solid stick preparations in particular, the invention discloses improved stick formulations that provide for delivery of water soluble therapeutic agents, non-water soluble agents, or both, upon topical application having improved drug stability.

In general, an object of these various stick formulations is to provide a physically and chemically stable solid formula in a stick preparation. Another object of the invention is to provide a stick having the following aesthetic qualities: ease of delivery, good spreadability, not easily washed from the skin, maintains solid state at temperatures below 42° C. and both physical and chemical stability of the incorporated drug.

Water Soluble Agent Containing Sticks

The stick formulations of the invention provide for convenient topical delivery of a water soluble therapeutic agent. In some embodiments, the stick comprises from about 30 to about 70% w/w wax (about 40 to about 50% w/w wax in particular embodiments), about 10 to about 55% w/w oil (about 15 to about 40% w/w oil in particular embodiments, or 30%), from about 1 to about 30% w/w water (about 3 to about 6% w/w water in particular embodiments), a surfactant and a water soluble therapeutic agent. In these preparations, as later described, the water soluble therapeutic agent is at least partially dissolved in water droplets, the water droplets being dispersed in the wax matrix of the stick.

In the preparation of the water soluble agent sticks, the agent is first dissolved in water and a surfactant added. A water in oil emulsion is created. This emulsion is added to and dispersed in the melted, cooled wax material of choice. In this manner, the water-soluble therapeutic agent is at least partially dissolved in water droplets dispersed throughout the wax based stick. Because it is a subsaturated solution, at least a part of the agent, and in some embodiments all of the active agent, is dissolved in the water droplets during the manufacturing and use of the product. The stability of the drug and the wax—The drug being dissolved in the water droplets as described.

The surfactant is further described as a w/o (water in oil) surfactant. In particular embodiments, the water in oil surfactant comprises about 0.2 to about 20% w/w, with other specific embodiments comprising between about 6 to 10%, or between about 2.5 to about 5% w/w. While any number of water in oil surfactants may be employed in the formulation, particular embodiments may be described as including a surfactant, WITCANOL® AMP.

The surfactant of the preparation provides enhanced stability of the drug in the stick. The surfactant may be any surfactant known in the art that will prevent the water droplets from separating. The surfactants are further defined as having a low HLB (hydrophobic lipophilic balance). A low HLB is defined for purposes of describing the present invention as not more than 9. By way of example, surfactants that may be used in the practice of the present invention include cholesterol, cholesterol esters, WITCANOL® APM, sorbitan trioleate, sorbitan tristearate, sorbitan sesquioleate, sorbitan monoleate, sorbitan monostearate, sorbitan monopalmitate, sorbitan monolaurate and glyceryl monostearate and the like. WITCANOL® APM is the surfactant of choice in particular embodiments.

Aquaphor® may be used instead of white petrolatum or other surfactant in particular embodiments. Because it contains cholesterol, this cholesterol acts as an emulsifier, negating necessity of adding other surfactants, to water soluble drug containing sticks. Other water in oil (w/o) emulsifying agents, such as hydrophilic petrolatum (USP), woolfat, lanolin, and lanolin derivatives, can be used instead of petrolatum in the stick preparations. Virtually any lipophilic material containing a w/o emulsifying agent may be employed in emulsifying the active agent, i.e., water soluble drug, prior to adding to the wax phase in formulating the sticks of the present invention.

The water soluble therapeutic agents of the sticks may include by way of example and not exclusion, antihistamines, local anesthetics, antibiotics, antifungal agents, anti-inflammatory agents, water soluble steroid salts, or a combination of these. Other embodiments of the stick may contain both a water soluble agent and a water insoluble agent.

A stick formulation containing a water soluble drug according to the present invention may be described as comprising about 30 to 46% w/w wax, about 12 to 20% w/w oil, about 6 to 19% (or about 6 to 10%) w/w surfactant, about 18 to 25% w/w semi-solid vehicle, about 1 to about 4% w/w bioadhesive oil soluble polymer, about 2 to 6% w/w water, about 0.025 to 4% w/w water soluble therapeutic agent, about 0.1 to 0.6% w/w antifungal agent and about 0.02 to 0.04% w/w/organic antioxidant.

Certain embodiments of the present invention may be described as stick formulations for the topical delivery of a water soluble therapeutic agent comprising about 17.4% w/w beeswax; about 12% w/w WITEPSOL® W35; about 16% w/w ceresin; about 9% w/w white petrolatum; about 7.5% w/w cetyl alcohol; about 9% w/w sesame oil; about 7.19% w/w mineral oil; about 5.5% w/w isopropyl myristate; about 8% w/w WITCONOL® APM; about 2% w/w Ganex V-220; about 4% w/w water; about 2.1% w/w diphenhydrámine hydrochloride; about 0.05% w/w Na$_2$EDTA; about 0.02% w/w BHA; about 0.02% w/w BHT; about 0.2% w/w methyl paraben; and about 0.02% w/w propyl paraben.

Another embodiment of the present invention may be described as a stick formulation for the topical delivery of a water soluble therapeutic agent comprising about 17.4% w/w beeswax; about 12% w/w WITEPSOL® W35; about 16% w/w ceresin; about 9% w/w white petrolatum; about 7.6% w/w cetyl alcohol; about 9% w/w sesame oil; about 7.19% w/w mineral oil; about 5.5% w/w isopropyl myristate; about 8% w/w WITCONOL® APM; about 2% w/w Ganex V-220; about 4% w/w water; about 2% w/w lidocaine hydrochloride; about 0.05% w/w Na$_2$EDTA; about 0.02% w/w BHA; about 0.02% w/w BHT; about 0.2% w/w methyl paraben; and about 0.02% w/w propyl paraben.

The stick formulations of the present invention that include water soluble agents, such as diphenhydramine hydrochloride, may be described generally as having the following characteristics:

1. A smooth, elegant, non-greasy delivery system for water soluble agents;
2. A solid water in oil emulsion system;
3. The water soluble agents are provided in solution in the water. Micron-size particles of the water soluble agent are contained in the aqueous solution and become dispersed throughout the wax stick to provide a combination micro (10 microns or 5 microns mean less) and macro (more than 10 microns mean particle diameter) emulsion of the aqueous solution in the wax(es) of the formulation. In this manner, the aqueous solution is dispersed as micro droplets throughout the stick.

4. Greater water soluble drug stability in the formulations. The water soluble active agent of the stick formulation is in an aqueous phase as part of an emulsion and then dispersed in the solid phase of the stick product. Direct contact between the water soluble drug and the solid phase components of the stick are thus prevented, avoiding any degradation that might be caused by such contact.

5. A characteristic low hydrophilic-lipophilic balance (HLB) surfactant (not greater than 9). In some embodiments, WHITCANOL® is employed. Other surfactants that may be employed by way of example, but not limitation, include sorbitan trioleate, sorbitan tristearate, sorbitan sesquioleate, sorbitan monoleate, sorbitan monostearate, sorbitan monopalmitate, sorbitan monolaurate and glyceryl monostearate (GMS). These and other agents that have a similarly low hydrophilic lypophilic balance (HLB) may function equally as surfactants in the water in oil emulsions disclosed herein.

Specific ingredients in some embodiments of the sticks that contain water soluble agents/drugs are:

Buffering agents, chelating agents, preservatives or stability enhancing agents, such as antioxidants, may be added to the aqueous phase during formulation. This feature permits one of skill in the art to customize a stick formulation to accommodate the particular chemical or physical characteristics of the water soluble drug desired.

Humectants. Humectants are hydroscopic materials that prevent water loss from the preparation. By way of example, such humectants include glycerin, propylene glycol, and polyethylene glycols.

Gelling agents. These gelling agents are more particularly described as aqueous gelling agents that are added to the aqueous phase during formulation to increase viscosity. Inclusion of a gelling agent in this matter will help decrease the evaporation of water form the product. Inclusion of a gelling agent will also permit the use of a higher w/w % of water in the preparation, relative to non-gelling agent containing preparations. By way of example, gelling agents that may be used in conjunction with the invention include: gelatin, PVP, PVA, cellulose derivatives (e.g., HPMC, HPC, HEC), acrylic derivatives (e.g., carboxymethyl cellulose, methyl cellulose and poly carbophil), natural and semi-synthetic polysaccharides (e.g., sodium alginate, chitosan, xanthan gum, acacia, carrageenan), inorganic gelling agents (veegum, bentonite), proteins (albumin, collagen), and aloe vera (as a thickening agent).

The water-in-oil emulsion employed in formulating the water-soluble drug containing sticks of the present invention have several advantages over the water soluble drug containing ointments and gels currently available. Some of these advantages include convenience of a stick application, improved spreadability on the skin, ability to carry water soluble additives, increased compatibility with human skin, and greater shelf life stability because of the unique dispersion of drug containing water droplets throughout the wax matrix of the formulation.

Non-Water Soluble Drug/Therapeutic Agent Containing Sticks

The invention also provides stick formulations for the delivery of non-water soluble therapeutic agents and drugs.

These stick formulations include the non-water soluble drug primarily in a dispersed form throughout the wax matrix of the stick. The therapeutic agent is therefore not necessarily dissolved in an oil prior to mixture with the wax of the stick.

The therapeutic agent/drug in some embodiments of the invention is of a small particle size, particularly described as "micronized" drug preparations. As used in the description of the present invention, the term micronized is defined as a drug preparation wherein at least part of the drug has a particle size diameter of about 10 microns, or even 5 microns, or less, in diameter. The non-water soluble therapeutic agent or drug as part of the stick formulation in some embodiments may be described as including primarily micronized size particles of the non-water soluble therapeutic agents or drugs. Particular non-water soluble therapeutic agents, by way of example, include hydrocortisone, retinoic acid derivatives, keratolytic agents (e.g., salicylic acid), miconazole, and antifungal agents.

Other of the stick formulations are formulated to provide topical delivery of asteroid. These particular embodiments comprise about 30 to about 70% w/w wax, from about 0.1 to about 40% w/w oil (or from 10% to 40% w/w oil), and from about 0.2 to 2% w/w non water soluble (i.e., lipophilic steroid), wherein the steroid is preferably a micronized preparation of hydrocortisone. In some embodiments, the wax is beeswax, ceresin, cetyl alcohol or a combination thereof. In still other embodiments, the oil is castor oil, mineral oil, sesame oil, isopropyl myristate or a combination thereof. The steroids or other non-water soluble agents of the stick may be further described as primarily dispersed throughout the wax matrix of the stick, rather than primarily dissolved in the oil.

Another embodiment of the invention is a stick formulation for topical delivery of hydrocortisone comprising about 10 to 20% w/w beeswax; about 6 to 10% w/w cetyl alcohol; about 6 to 15% w/w mineral oil; about 10 to 20% w/w ceresin wax; about 8 to 14% w/w isopropyl myristate; about 0.2 to 2.0% w/w (or about 1.07% w/w) micronized hydrocortisone; and about 10 to 20% w/w sesame oil. This stick formulation may also be described as comprising one or more of about 8 to 10% w/w white petrolatum, about 10 to 15% w/w WITEPSOL®, and/or about 3 to 10% w/w of a bioadhesive oil soluble polymer. An example of such a bioadhesive oil soluble polymer is Ganex V-216 or Ganex V-220.

An alternative stick formulation for topical delivery of hydrocortisone may comprise about 11.8% w/w cocoa butter; about 15 to 16% w/w beeswax; about 9.3% w/w white petrolatum; about 8.3% w/w cetyl alcohol; about 14.8% w/w castor oil; about 10.5% w/w mineral oil; about 17.1% w/w ceresin; about 11.6% w/w isopropyl myristate; about 1.1% w/w water insoluble therapeutic agent; about 0.2% w/w disodium EDTA; about 0.02% w/w BHT; and about 0.02% w/w BHA. Preferably, at least part of the water insoluble therapeutic agent is in micron size particles, that is, having a mean particle diameter of 10 microns, or even 5 microns in a particular embodiment, the water insoluble agent is hydrocortisone, and is included in the stick in a micronized hydrocortisone preparation.

Yet another stick formulation may comprise about 11.84% w/w cocoa butter; about 15.7% w/w beeswax; about 9.3% w/w white petrolatum; about 8.3% w/w cetyl alcohol; about 14.8% w/w castor oil; about 11% w/w mineral oil; about 17.1% w/w ceresin; about 11.6% w/w isopropyl myristate; about 0.1% w/w triamcinolone acetonide; about 0.2% w/w disodium EDTA; about 0.02% w/w BHT; and about 0.02% w/w BHA.

Another embodiment of the stick invention may comprise about 11.4% w/w cocoa butter; about 22.5% w/w beeswax; about 17.5% w/w ceresin; about 8.3% w/w cetyl alcohol; about 14.4% w/w sesame oil; about 11.9% w/w mineral oil; about 12.8% w/w isopropyl myristate; about 0.02% w/w BHA; and about 1% (1.07%) w/w hydrocortisone. Other embodiments of the hydrocortisone stick comprise: about 1 to about 12% WITEPSOL® 35 pellets, about 13–17% w/w beeswax, about 9–10% w/w petrolatum, about 7 to about 8.5% w/w cetyl alcohol, about 12–18% w/w sesame oil, about 6 to about 9% w/w mineral oil, about 12 to about 17% w/w ceresin about 12 to 13% w/w is propyl myristate, and about 1% (or 1.07%) w/w hydrocortisone.

Further defined, this stick formulation may comprise about 11.8% w/w WITEPSOL® W35 pellets; about 16.3% w/w beeswax; about 9.4% w/w white petrolatum; about 8.3% w/w cetyl alcohol; about 14.7% w/w sesame oil; about 8.5% w/w mineral oil; about 17.1% w/w ceresin; about 12.8% w/w isopropyl myristate; and about 1% (1.06% or 1.07%) w/w hydrocortisone. An even further embodiment of said stick formulation may comprise about 11.8% w/w WITEPSOL® W35 pellets; about 15% w/w beeswax; about 9.3% w/w white petrolatum; about 8.3% w/w cetyl alcohol; about 12.8% w/w sesame oil; about 8.5% w/w mineral oil; about 17.1% w/w ceresin; about 12.6% w/w isopropyl myristate; about 1% (or 1.07%) w/w hydrocortisone; and about 3.5% w/w Ganex V-216. Other of the stick preparations may comprise about 12.1% w/w WITEPSOL® pellets; about 14.5% w/w beeswax; about 9% w/w white petrolatum; about 7.5% w/w cetyl alcohol; about 12.8% w/w sesame oil; about 7% w/w mineral oil; about 16% w/w ceresin; about 11.6% w/w isopropyl myristate; about 1% (or 1.07%) w/w hydrocortisone; and about 8.5% w/w Ganex V-216.

Further stick formulations for topical delivery of hydrocortisone may comprise about 12.1% w/w WITEPSOL® W35 pellets; about 14.5% w/w beeswax; about 9% w/w white petrolatum; about 7.5% w/w cetyl alcohol; about 12.8% w/w sesame oil; about 6.8% w/w mineral oil; about 16% w/w ceresin; about 11.6% w/w isopropyl myristate; about 1% (or 1.07%) w/w hydrocortisone; about 8.5% w/w Ganex V-216; and about 0.2% w/w vitamin E. The stick preparation may also further include BHA, such as in an amount of about 0.02% w/w.

Stick formulations for topical delivery of hydrocortisone of the present invention may also comprise about 12% w/w WITEPSOL® W35 pellets; about 13% w/w beeswax; about 9% w/w white petrolatum; about 7.3% w/w cetyl alcohol; about 17.3% w/w sesame oil; about 6.9% w/w mineral oil; about 13% (or 12.9%) w/w ceresin; about 12% w/w isopropyl myristate; about 1.07% w/w hydrocortisone; about 8.5% w/w Ganex V-216; and about 0.02% w/w BHA. The invention also provides for an ethanol based hydrocortisone stick. This particular stick comprises hydrocortisone (preferably micronized hydrocortisone) (preferably at a concentration of between 0.2 to 1.0% w/w, or 0.5% w/w), sodium stearate (preferably at a concentration of about 10 to 15 w/w, or 12.0% w/w), ethanol (preferably between 30.00 to about 50% w/w, or about 40.0% w/w), propylene glycol (preferably between 20.0 to 40.0% w/w), and 30.0% w/w and water (preferably about 15 to about 20% w/w, or about 17.4% w/w).

Specific ingredients in some embodiments of the sticks that contain the non-water soluble drugs include:

sesame oil—and other vegetable oils, which contain natural antioxidants;

Miglyol—promotes absorption and improves the efficiency of the product. A mix of sesame oil and miglyol may also be employed in some stick embodiments;

presence of WITEPSOL® waxes, or other similar waxes which are mixtures of mono, di- and triglycerides. These materials prevent the separation of the oils and the waxes in the final formulation;

a bioadhesive polymer, for example, 2 pyrrolidinone,1 ethenyl-polymer with 1-trochantine (Ganex) or 2 butanedioic acid (z)-, polymer with methoxyethene, calcium and sodium salt (Gantrez) which improves spreadability and contributes to the hydrophobic properties of the product that prevent the product from being washed from the skin;

Hydrocortisone or other micronized non-water soluble drug readily dispersable in a molten base. The small particle size of the drug also insures good content uniformity in the finished product;

cocoa butter (theobroma oil) improves the spreadability and aesthetic feel.

Water Soluble and Non-Water Soluble Therapeutic Agent Containing Sticks

The present invention also provides for stick formulations that include both a water soluble therapeutic agent and a non-water soluble therapeutic agent in a stick formulation. In these preparations, the water soluble drug is dissolved in water and the water droplets dispersed throughout the wax matrix of the stick. The non-water soluble drug is dispersed directly in the wax matrix.

By way of example, such a stick would include the water soluble agent, diphenhydramine hydrocloride, and the non-water soluble agent, hydrocortisone. Other combinations of agents may also be formulated. The stick formulation may also comprise a semi-solid vehicle in order to improve the aesthetic feel of the stick and to improve spreadability. Such semi-solid vehicles will preferably have a melting point between about 38° C. and about 60° C. Preferred semi-solid vehicles include, but are not limited to cocoa butter, white petrolatum, WITEPSOL® or more preferably a combination of these. Other ingredients that may be added to the sticks include organic antioxidants such as BHT and BHA, preservatives such as methyl paraben or propyl paraben and chelators such as $Na_2EDTA$, or even ascorbic acid, vitamin C or vitamin E.

Particular water soluble agents that may be used in the claimed invention include diphenhydramine hydrochloride, lidocaine hydrochloride, triamcinolone acetonide dipotassium phosphate (a soluble phosphate salt) and dexamethasone sodium phosphate. Any of the foredescribed non-water soluble agents may be incorporated into the combination stick according to the present invention.

Wax Materials

The waxes that may be used to prepare the sticks of both the water soluble and non-water soluble agents are chosen so that the sticks can be prepared without subjecting the active agents to high temperatures. Preferred waxes include, but are not limited to beeswax, stearyl alcohol, ceto-stearyl alcohol, paraffin, gelucires (mono, di, and tri glycerides), precirol (hydrophilic waxes that include mono and di glycerides act to absorb small quantities of water), ceresin, cetyl alcohol, WITEPSOL® W35 or a combination of these. The oils that may be used in the sticks include by way of example, vegetable oil, sesame oil, mineral oil, castor oil, soybean oil, sunflower oil, peanut oil, cottonseed oil, isopropyl myristate or a combination of these.

Methods

The present invention also provides a method of producing a stick formulation for topical delivery of a water soluble agent comprising the steps of mixing an oil or mixture of oils and oil soluble bioadhesive polymer to provide a first mixture and stirring, mixing a water soluble agent and water together with a surfactant to provide a second mixture (in some embodiments, such that no more than 50% saturation is achieved), stirring, preferably for about 10 minutes, adding the first mixture to the second mixture and stirring vigorously for 15 to 20 minutes to provide a third mixture; combining an appropriate amount of wax and semi-solid vehicle and heating and stirring until the wax has melted to form a fourth mixture; warming the fourth mixture to 50°–55° C.; combining the third mixture with the fourth mixture to form a fifth mixture and preparing sticks of said fourth mixture by pouring the fifth mixture into molds suitable for forming sticks.

In preferred embodiments of the method, the oil is sesame oil, mineral oil, isopropyl myristate or a combination of these; the oil soluble bioadhesive polymer is Ganex V-216 or Ganex V-220; and the water soluble agent is diphenhydramine hydrochloride.

This method of preparing these water soluble drug containing sticks may further comprise the step of dissolving at least one additional ingredient, an organic antioxidant or preservative, with the surfactant prior to adding said surfactant to the second mixture. Such organic antioxidants include BHA, BHT, methyl paraben, propyl paraben or a combination of these. In certain preferred embodiments of the method, the surfactant is WITCANOL® APM; the wax is beeswax, WITEPSOL® W35, ceresin, cetyl alcohol or a combination thereof; and the semi-solid vehicle is white petrolatum. A stick formulation produced by this method is also an embodiment of the invention.

Methods for preparing a wax based stick containing a water-insoluble therapeutic agent or drug are also provided, as well as products produced by these methods. In particular embodiments, the drug is hydrocortisone. In one embodiment, a particular process comprises preparing a first mixture of an oil or mixture of oils together with waxes; heating the first mixture sufficiently to melt at least part of the waxes; adding a water insoluble agent to the first mixture to provide a second mixture, and preparing sticks of the second mixture to provide a wax-based stick. In particular embodiments, the water insoluble agent is hydrocortisone. In the final product, hydrocortisone is preferably included at a concentration of about 1% (or about 1.07%) w/w of the stick.

DETAILED DESCRIPTION OF THE PREFERRED EMBODIMENTS

Figure 1:
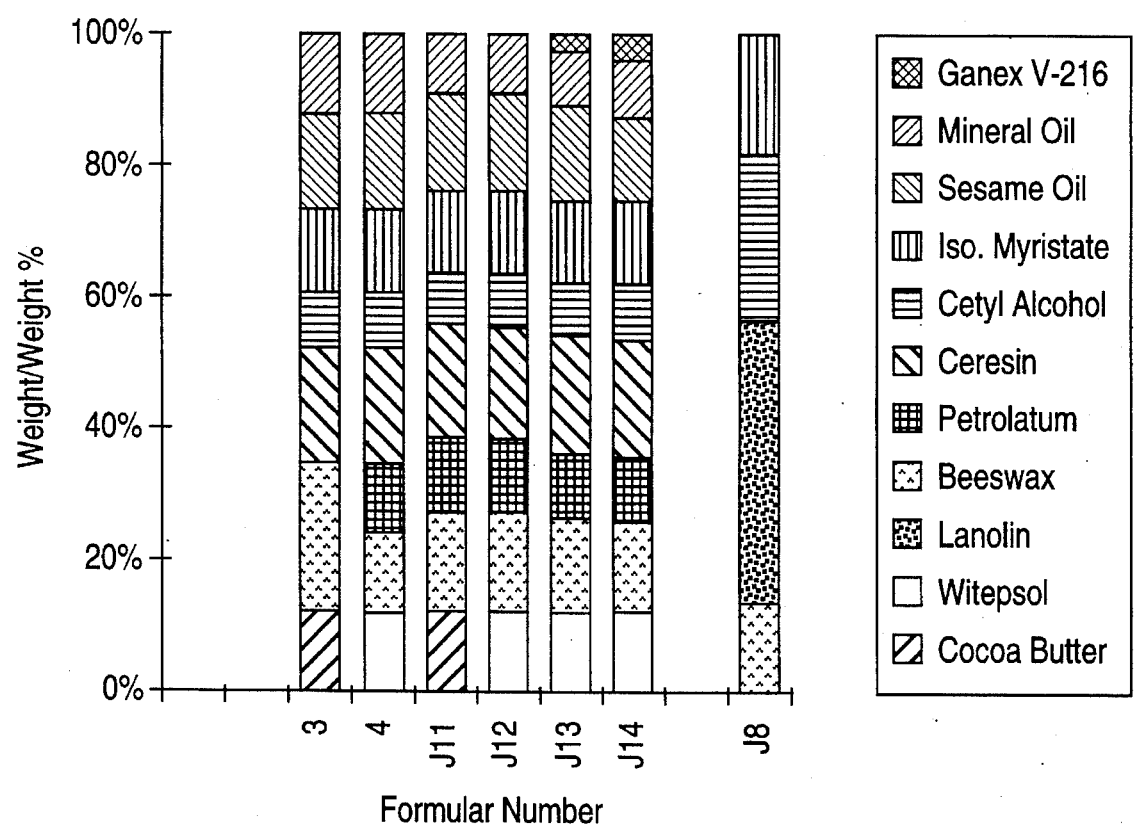
Figure 2:
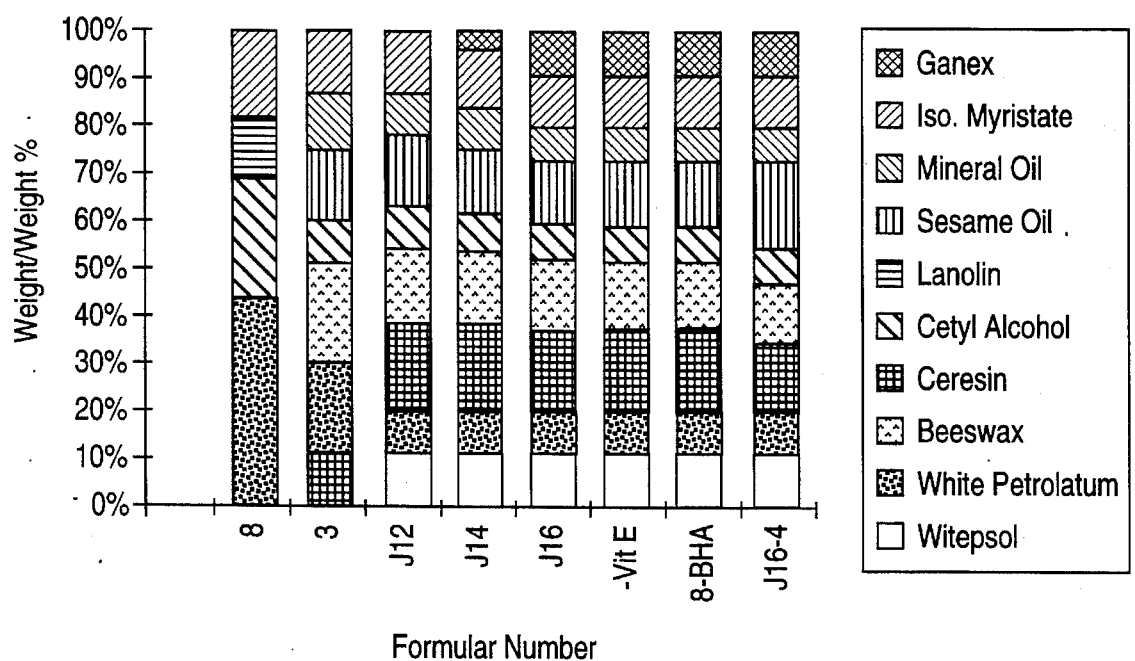

The present invention relates to the delivery of water soluble and water insoluble therapeutic agents in a stick preparation. Such water soluble agents include, by way of example, anti-inflammatory agents, local anesthetics, antibiotics and other topical therapeutic agents. The water-insoluble agents include, by example, hydrocortisone. The invention thus provides a stick useful in the application of these and other therapeutic agents (drugs) to skin and various mucosal surfaces of the body with the convenience of a solid stick formulation. The novel delivery systems of the present invention provide availability of water soluble or water insoluble agents that are physically and chemically stable.

The present invention provides in part, stick formulations that may be used for the relief of itching associated with eczema, psoriasis, insect bites, poison ivy and other skin irritations. One embodiment of the invention is a wax based stick formula containing dispersed hydrocortisone for topical administration. Rather than being solubilized or partially solubilized, or dissolved in an oil; the hydrocortisone is micronized and dispersed in the wax. Relatively high concentrations of hydrocortisone can be incorporated in the stick with retained skin compatibility. In some embodiments, the hydrocortisone stick contains little to no carnauba wax or other high melting point wax. This, the active ingredient, such as a steroid, is not subjected to the high temperatures necessary to melt such waxes. In addition, the wax has less tendency to agglomerate on cooling. In addition, the hydrocortisone stick of the present invention contains cocoa butter for a smoother spreadability and a less waxy feeling on the skin.

The stick formulations with water soluble drugs comprise water soluble drugs that are primarily contained in small water droplets dispersed in a wax stick. The water droplets may optionally contain buffers, salts or other compounds that contribute to the stability and effectiveness of the drug.

In a general sense, the water-soluble drug containing sticks are prepared from formulations that comprise from about 30% to about 70% w/w (or 40% to 50%) of a wax (such as beeswax, ceresin, cetyl alcohol, WITEPSOL®, acetyl alcohol, stearyl alcohol, cetostearyl alcohol, stearic acid or a combination of these), from about 1% to about 40% w/w (or about 10% to 30%) of an oil (such as sesame oil, mygliol, peanut oil, cotton seed oil, safflower oil, cod liver oil, mineral oil, castor oil, lanolin, isopropyl myristate, other fixed oil, or a combination of these), and a surfactant (such as low HLB surfactants, Witcanol, sorbitan trioleate, sorbitan tristearate, sorbitan sesquioleate, sorbitan monooleate, sorbitan monostearate, sorbitan monopalmitate, sorbitan monolaurate, glyceryl monostearate, cholesterol or a combination of these).

The water soluble active ingredients of the formulations include, but are not limited to water soluble steroids, antihistamines (e.g., diphenhydramine hydrochloride), antibiotics, antifungals and local anesthetics.

Non-water soluble drugs and therapeutic agents that may be used in the invention include hydrocortisone, citronella oil, cortisol acetate, betamethasone benzoate, betamethasone dipropionate, betamethasone valerate, dexamethasone, methylprednisolone acetate, triamcinolone acetonide, alclometasone dipropionate, amcinonide, clobetasol propionate, clocortolone pivalate, cortisol butyrate, cortisol valerate, desonide, desoximetasone, diflorasone diacetate, fluocinolone acetonide, halcinonide, mometasone furoate, non-water soluble antifungal agents (e.g., tercanazole, nystatin), retinoic acid derivatives (e.g., tretinoin), and keratolytic agents (e.g., salicylic acid). Hydrocortisone being the most preferred.

Ibuprofen and indomethacin are other agents that may be included in the sticks of the present invention. Water soluble drugs useful in the stick formulations, by way of example, include lidocaine hydrochloride, tetracaine hydrochloride dibucaine hydrochloride, dyclonine hydrochloride, miconazole nitrate, pramoxine hydrochloride, dexamethasone sodium phosphate, and the like.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Water-Insoluble Drug Containing Sticks

The following procedure was used in the formulation of the hydrocortisone sticks in the following examples: 1,2,6, and 8–16. This procedure may be used in the formulation of sticks containing other non-water soluble therapeutic agents of the invention as well.

1. Weigh mineral oil, castor oil and isopropyl myristate into beaker.
2. Add BHA, BHT and Na$_2$EDTA, stir.
3. Add all other ingredients (beeswax, cocoa butter, white petrolatum, cetyl alcohol, ceresin) except hydrocortisone.
4. Heat to 60°–65° C. while stirring.
5. When melted, cool to 55° C., add the water insoluble drug (such as hydrocortisone) and stir until dispersed.
6. Pour into molds suitable for forming sticks.

In the stick preparations containing water insoluble agents, such as hydrocortisone, the drug is not first dissolved in an oil prior to addition of the wax and other components of the preparation. Instead, the agent (steroid) is mixed together with the cooled, molten wax and any other ingredient to be included with the preparation. Such provides a stick wherein the non-water soluble agent (drug) is dispersed throughout the wax of the stick without being dissolved in an oil. Micronized non-water soluble drugs, (i.e., drugs having a mean particle size of 10 or even 5 microns or less) are particularly preferred, and provide a dispersion of the drug, such as hydrocortisone, throughout the wax matrix that is compatible with skin contact.

In the following formulations, the total w/w content may not be equal to exactly 100%. This may be due in part to the addition of an excess of active agent in the stick formulations in order to ensure that a sufficient amount of the agent is available for topical delivery. As is well known in the art, up to 110% of the amount of active ingredient on the label may be added to the formulation.

EXAMPLE 1

Hydrocortisone Stick

| Chemical | w/w % |
| --- | --- |
| cocoa butter | 11.840 |
| beeswax | 15.294 |
| white petrolatum | 9.320 |
| cetyl alcohol | 8.320 |
| castor oil | 14.780 |
| mineral oil | 10.480 |
| ceresin | 17.110 |
| isopropyl myristate | 11.590 |
| hydrocortisone (micronized) | 1.060 |
| disodium EDTA | 0.200 |
| BHT | 0.020 |
| BHA | 0.020 |

The stick was formulated as described above. The hydrocortisone is in a dispersed state throughout the wax maxtrix. This formulation/method may be used in preparing other steroid containing sticks other than hydrocortisone, at about 1.0% w/w.

EXAMPLE 2

Steroid Stick

The stick was formulated essentially as described in Example 1, substituting triamcinolone acetonide for hydrocortisone.

| Chemical | w/w % |
|---|---|
| cocoa butter | 11.840 |
| beeswax | 15.750 |
| white petrolatum | 9.320 |
| cetyl alcohol | 8.320 |
| castor oil | 14.780 |
| mineral oil | 10.980 |
| ceresin | 17.110 |
| isopropyl myristate | 11.590 |
| triamcinolone acetonide | 0.1 |
| disodium EDTA | 0.200 |
| BHT | 0.020 |
| BHA | 0.020 |

EXAMPLE 3

Diphenhydramine Hydrochloride Stick

| Chemical | w/w % |
|---|---|
| beeswax | 17.40 |
| WITEPSOL ® W35 | 12.00 |
| ceresin | 16.00 |
| white petrolatum | 9.00 |
| cetyl alcohol | 7.50 |
| sesame oil | 9.00 |
| mineral oil | 7.19 |
| isopropyl myristate | 5.50 |
| WITCONOL ® APM | 8.00 |
| Ganex V-220 | 2.00 |
| water | 4.00 |
| diphenhydramine hydrochloride | 2.10 |
| Na$_2$EDTA | 0.05 |
| BHA | 0.02 |
| BHT | 0.02 |
| methyl paraben | 0.20 |
| propyl paraben | 0.02 |

The following procedure was employed in the preparation of the diphenhydramine containing stick. Other water soluble agents may be formulated into a stick using primarily the same protocol, by substituting the diphenhydramine for the agent of interest.

Procedure

1. Weigh sesame oil, mineral oil, isopropyl myristate and Ganex V-220 into Beaker A and stir.
2. In a separate beaker (B), dissolve diphenhydramine hydrochloride in water.
3. Dissolve BHT, BHA, methyl paraben and propyl paraben in WITCONOL® APM (Beaker C).
4. Add contents of Beaker C to Beaker B, stir for about 10 minutes.
5. Add contents of Beaker B to Beaker A, stir vigorously for about 15 to about 20 minutes.
6. Weigh out beeswax, WITEPSOL® W35, ceresin, white petrolatum, cetyl alcohol and Na$_2$EDTA, heat and stir until all wax has melted and add to Beaker A, that has been warmed to 50°–55° C.
7. Pour into molds suitable for forming sticks.

The diphenhydramine is dissolved in water prior to addition to the melted and cooled wax mixture, and becomes dispersed inside tiny water droplets throughout the wax matrix. The drug is at least partially insulated within the water droplets from degradative processes of the surrounding wax and other ingredients in the wax.

EXAMPLE 4

Lidocaine Stick

| Chemical | w/w % |
|---|---|
| beeswax | 17.40 |
| WITEPSOL ® W35 | 12.00 |
| ceresin | 16.00 |
| white petrolatum | 9.00 |
| cetyl alcohol | 7.60 |
| sesame oil | 9.00 |
| mineral oil | 7.19 |
| isopropyl myristate | 5.50 |
| WITCONOL ® APM | 8.00 |
| Ganex V-220 | 2.00 |
| water | 4.00 |
| Lidocaine hydrochloride | 2.00 |
| Na$_2$EDTA | 0.05 |
| BHA | 0.02 |
| BHT | 0.02 |
| methyl paraben | 0.20 |
| propyl paraben | 0.02 |

The stick formulation of this example is prepared in accordance with the procedure of Example 3. Na$_2$EDTA is not included, and lidocaine hydrochloride (micronized) is substituted for diphenhydramine hydrochloride.

EXAMPLE 5

Hydrocortisone and Diphenhydramine Hydrochloride Stick

| Chemical | w/w % |
|---|---|
| beeswax | 17.40 |
| WITEPSOL ® W35 | 12.00 |
| ceresin | 16.00 |
| white petrolatum | 9.00 |
| cetyl alcohol | 7.50 |
| sesame oil | 9.00 |
| mineral oil | 6.19 |
| isopropyl myristate | 5.50 |
| WITCONOL ® APM | 8.00 |
| Ganex V-216 | 2.00 |
| water | 4.00 |
| diphenhydramine hydrochloride | 2.10 |
| hydrocortisone (micronized) | 1.00 |
| Na$_2$EDTA | 0.05 |
| BHA | 0.02 |
| BHT | 0.02 |
| methyl paraben | 0.20 |
| propyl paraben | 0.02 |

Procedure

1. Weigh sesame oil, mineral oil, isopropyl myristate and Ganex V-216 (or Ganex V-220) into Beaker A and stir.
2. In a separate beaker B, dissolve diphenhydramine hydrochloride in water.
3. Dissolve BHT, BHA, methyl paraben and propyl paraben in WITCONOL® APM (Beaker C).
4. Add contents of Beaker C to Beaker B, stir for 10 minutes.
5. Add contents of Beaker B to Beaker A, stir vigorously for 15 to 20 minutes.
6. Weigh out beeswax, WITEPSOL® W35, ceresin, white petrolatum, cetyl alcohol and Na$_2$EDTA, heat and stir until all wax has melted, add hydrocortisone and add to Beaker A, that has been warmed to 50°–55° C.
7. Pour into molds suitable for forming sticks.

Other combinations that may be used in the combination stick formulations of the present invention include:

1. triamcinolone acetonide (1% w/w) (dispersed phase) and diphenhydramine (or other water soluble agent);
2. lidocaine hydrochloride (aqueous) (2% w/w) and triamcinolone acetonide (0.1% w/w);
3. triamcinolone acetonide diphosphaestum phosphate (0.05% w/w) (aqueous phase) and triamcinolone acetonide (0.05% w/w) (in dispersion);
4. tretinoin (a retinoic acid derivative) (0.05% w/w, dispersed oil phase) and lidocaine hydrochloride (2% w/w, aqueous phase); and
5. miconazole nitrate (aqueous phase; 2% w/w)+betamethasone dipropionate (in dispersed phase) 0.05% w/w).

EXAMPLE 6

Stick Formulation Testing

Stability procedure

The procedure for testing stability requires the preparation of 200 sticks of each sample formulation. The samples are tested at 40° C., ambient temperature and 40° C./75% relative humidity. The times at which data are taken are 0, 2 weeks, 1 month, 2 months, and 3 months. Long-term data collection time points are 6 months, 1 year, 2 years and 3 years. Four sticks are placed at each data point, two for the HPLC assay and two for assessment of physical characteristics.

Stability Formulations

Different formulations are tested and compared for stability. Groups for comparison include wax/oil base and propylene glycol/WITCONOL® APM base (clear stick). A further comparison point between the clear stick formulas is the addition of Witcamide 128T, a surfactant. There are several points of comparison among the wax/oil formulas. Cocoa butter and WITEPSOL® W35 are two waxes to be compared on the basis of their effect on the texture and color of the stick. The levels of Ganex V-216 in formulations are varied, from 0%, to 3.5%, to 8.5% to study the effect of the Ganex on the stability of the hydrocortisone, if any. The effectiveness of antioxidants vitamin E and BHA are also compared as well as sesame oil and its natural antioxidants. Lastly, the wax/oil ratio is varied in order to affect the softness of the stick.

HPLC tests

For testing of hydrocortisone stick formulations, the samples were prepared as follows:

a) approximately 100 mg of the spatulated wax stick was weighed accurately into a 20 ml vial and 10 ml of tetrahydrofuran was added;
b) samples were shaken and sonicated for at least 15 minutes until all material was dissolved;
c) samples were filtered through 0.45 μm teflon filters and aliquots were injected into the HPLC.

The use of HPLC columns is well known in the art and any such column such as a C 18 column for example would be suitable for the tests described herein. Approximately 10 μl samples are routinely injected into HPLC and the mobil phase may be adjusted by increasing or decreasing the amount of acetonitrile in the buffer to give good separation of sample components. Absorption at 242 nm is measured for hydrocortisone sticks and at 254 nm for diphenhydramine sticks.

For testing of diphenhydramine stick formulations, the samples were prepared as follows:

a) approximately 100 mg of the spatulated wax stick was weighed accurately into a 20 ml vial and 2 ml of tetrahydrofuran was added;
b) samples were shaken and sonicated for at least 15 minutes until all material was dissolved;
c) samples were cooled in a refrigerator and 8 ml of water was added to precipitate the waxes;
d) samples were filtered through 0.45 μm teflon filters and aliquots were injected into the HPLC.

Three samples were tested for each stick formulation. Tetrahydrofuran blanks were run at the beginning and end of each testing period. If the testing period was more than 12 hours, a standard calibration was run in the middle of the run. The columns were rinsed for a minimum of 2 hours at the end of a run.

The optimal pouring temperature was determined to be about 55° C., in order to avoid having the hydrocortisone exposed to higher temperatures and to avoid air bubbles or incomplete filling of the molds such as might occur when pouring at lower temperatures. Also, in order to assure the presence of 1% hydrocortisone in the final product the amount of hydrocortisone in the formula was increased to 1.07%.

EXAMPLE 7

Ethanol Based Hydrocortisone Stick

| Chemical | w/w % |
| --- | --- |
| hydrocortisone | 0.5 |
| sodium stearate | 12.0 |
| ethanol | 40.0 |
| propylene glycol | 30.0 |
| water | 17.5 |

Procedure

1. Dissolve sodium stearate in hot water (75° C.).
2. Dissolve hydrocortisone in ethanol and propylene glycol.
3. Mix the two phases together and cast into molds.

EXAMPLE 8

Hydrocortisone Stick Formula 3

The following stick was formulated as described supra. Particular proportions of ingredients have been changed.

| Chemical | w/w % |
| --- | --- |
| cocoa butter | 11.40 |
| beeswax | 22.54 |
| ceresin | 17.52 |
| cetyl alcohol | 8.34 |
| sesame oil | 14.42 |
| mineral oil | 11.86 |
| isopropyl myristate | 12.83 |
| BHA | 0.02 |
| hydrocortisone | 1.07 |

EXAMPLE 9

Hydrocortisone Stick Formula 4

| Chemical | w/w % |
| --- | --- |
| WITEPSOL ® W35 pellets | 11.84 |
| beeswax | 16.30 |
| white petrolatum | 9.38 |
| cetyl alcohol | 8.30 |
| sesame oil | 14.72 |
| mineral oil | 8.54 |
| ceresin | 17.10 |
| isopropyl myristate | 12.75 |
| hydrocortisone | 1.07 |

EXAMPLE 10

Hydrocortisone Stick Formula 5

| Chemical | w/w % |
| --- | --- |
| sesame oil | 12.80 |
| mineral oil | 8.54 |
| isopropyl myristate | 12.60 |
| WITEPSOL ® W35 pellets | 11.84 |
| beeswax | 14.95 |
| ceresin | 17.10 |
| cetyl alcohol | 8.30 |
| white petrolatum | 9.30 |
| hydrocortisone | 1.07 |
| Ganex V-216 | 3.50 |

EXAMPLE 11

Hydrocortisone Stick Formula 6

| Chemical | w/w % |
| --- | --- |
| sesame oil | 12.75 |
| mineral oil | 7.00 |
| isopropyl myristate | 11.58 |
| WITEPSOL ® W35 pellets | 12.10 |
| beeswax | 14.50 |
| ceresin | 16.00 |
| cetyl alcohol | 7.50 |
| white petrolatum | 9.00 |
| hydrocortisone | 1.07 |
| Ganex V-216 | 8.50 |

EXAMPLE 12

Hydrocortisone Stick Formula 7

| Chemical | w/w % |
| --- | --- |
| sesame oil | 12.75 |
| mineral oil | 6.80 |
| isopropyl myristate | 11.58 |
| WITEPSOL ® W35 pellets | 12.10 |
| beeswax | 14.50 |
| ceresin | 16.00 |
| cetyl alcohol | 7.50 |
| white petrolatum | 9.00 |
| hydrocortisone | 1.07 |
| Ganex V-216 | 8.50 |
| Vitamin E | 0.20 |

EXAMPLE 13

Hydrocortisone Stick Formula 8

| Chemical | w/w % |
| --- | --- |
| sesame oil | 12.75 |
| mineral oil | 6.98 |
| isopropyl myristate | 11.58 |
| WITEPSOL ® W35 pellets | 12.10 |
| beeswax | 14.50 |
| ceresin | 16.00 |
| cetyl alcohol | 7.50 |
| white petrolatum | 9.00 |
| hydrocortisone | 1.07 |
| Ganex V-216 | 8.50 |
| BHA | 0.02 |

EXAMPLE 14

Hydrocortisone Stick Formula 9

| Chemical | w/w % |
| --- | --- |
| sesame oil | 17.34 |
| mineral oil | 6.92 |
| isopropyl myristate | 12.00 |
| WITEPSOL ® W35 pellets | 12.00 |
| beeswax | 13.00 |
| ceresin | 12.90 |
| cetyl alcohol | 7.25 |
| white petrolatum | 9.00 |
| hydrocortisone | 1.07 |
| Ganex V-216 | 8.50 |
| BHA | 0.02 |

EXAMPLE 15

Hydrocortisone Stick Formula 10

| Chemical | w/w % |
| --- | --- |
| sodium stearate | 11.4 |
| propylene glycol | 28.5 |
| water | 7.6 |
| WITCONOL ® APM | 42.81 |
| Witcamide 128T | 8.6 |
| hydrocortisone | 1.07 |
| BHA | 0.02 |

EXAMPLE 16

Hydrocortisone Stick Formula 11

| Chemical | w/w % |
| --- | --- |
| sodium stearate | 11.6 |
| propylene glycol | 34.4 |
| water | 12.01 |
| WITCONOL ® APM | 40.9 |
| hydrocortisone | 1.07 |
| BHA | 0.02 |

EXAMPLE 17

Water Soluble Drug Sticks

The present example is provided to demonstrate the utility of the present invention in the preparation of stick formulations that include water soluble therapeutic agents. By way of example, such water soluble therapeutic agents may include lidocaine hydrochloride or other local anesthetics, antibiotics, antihistamines and anti inflammatory agents, antifungal agents and the like.

The stick preparations provide for topical delivery of these water soluble therapeutic agents. These water soluble therapeutic agents are dispersed throughout the wax carrier provided in the stick formulation. The water soluble therapeutic agent is primarily in a water in oil (w/o) emulsion, to provide an essentially crystal-free dispersion of the therapeutic agent.

Such formulations would be useful in the treatment of insect bites, cuts, abrasions, allergic reactions, fungal infections, sunburn, and other minor skin irritations.

EXAMPLE 18

DIPHENHYDRAMINE HYDROCHLORIDE STICK

The present example provides a formulation employing Aquaphor® (a commercial product) as the surfactant to be used together with a water soluble drug, such as diphenhydramine hydrochloride. In these formulations, Aquaphor® is used instead of other surfactants, and white petrolatum may be omitted. Aquaphor® contains cholesterol. Cholesterol acts as an emulsifier, and makes the addition of other surfactants to the water soluble drug containing sticks unnecessary.

| Chemical | w/w % |
|---|---|
| Beeswax | 17.4 |
| WITEPSOL ® W35 | 12.0 |
| ceresin | 16.00 |
| cetyl alcohol | 7.50 |
| sesame oil | 9.00 |
| mineral oil | 11.19 |
| isopropyl myristate | 5.50 |
| Ganex V-220 | 2.00 |
| water | 4.00 |
| diphenhydramine hydrochloride | 2.10 |
| $Na_2$ EDTA | 0.05 |
| BHA | 0.02 |
| BHT | 0.02 |
| Aquaphor ® | 13.00 |
| Methylparaben | 0.20 |
| propyl paraben | 0.02 |

Procedure:

1. Weight sesame oil, mineral oil,l and Ganex V-216 into Beaker A and stir.

2. In a separate beaker (B), dissolve diphenhydramine hydrochloride in water.

3. Dissolve BHT, BHA, methyl paraben and propyl paraben with the isopropyl myristate (Beaker C).

4. Add contents of Beaker C to Beaker B, stir for about 20 minutes.

5. Add contents of Beaker B to Beaker A, stir vigorously for about 15 to about 20 minutes.

6. Weight out beeswax, WITEPSOL® W35, ceresin, Aquaphor®, cetyl alcohol and $Na_2$ EDTA, heat and stir until all wax has melted and add to Beaker A, that has been warmed to 50°–55° C.

7. Pour into molds suitable for forming sticks.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Assasy et al. (1976), Cosmetics and Toiletries, 91:54–56
Barker G. (1977), Cosmetics and Toiletries, 92:81–86
Barker, G. (1977), Cosmetics and Toiletries, 92:73–75
Barker, G. (1987), Cosmetics and Toiletries, 102:71–80
Barker et al. (1982), Soap/Cosmetics/Chemical Specialties, 44A–44B
Bozic et al. (1980), Cosmetics and Toiletries, 95:54–56
Carlson, B. C. (1977), Cosmetics and Toiletries, 92:81–86
Chang, I. B. (1977), Cosmetics and Toiletries 92:25–26
Cosmetics and Toiletries, 92:54–64.
Cosmetics and Toiletries (1987), 102: 53–63
DeRagon et al. (1977), Cosmetics and Toiletries, 92:39–41
Fox, Charles (1984), Cosmetics and Toiletries, 99:19–54
Fox, Charles (1987), Cosmetics and Toiletries, 102:33–53
Fukasawa et al. (1988), Cosmetics and Toiletries, 103:78–79
Geria, Nayin (1987), Cosmetics and Toiletries, 102:65–70
Korbar-Smid et al. (1978), Cosmetics and Toiletries, 93:33–34
Neulinger, Kurt (1977), Cosmetics and Toiletries, 92:65–67
Prosserpio et al. (1975), Cosmetics and Perfumery, 90:41–42
Schmolka, Irving (1977), Cosmetics and Toiletries, 92:77–79
Schmolka, Irving (1984), Cosmetics and Toiletries, 99:69–76
Teng et al. (1975), Cosmetics and Perfumery, 90:33–42
Teng et al. (1977), Cosmetics and Toiletries, 92:39–40
Vaughan et al. (1977), Cosmetics and Toiletries, 92:47–53
U.S. Pat. No. 4,048,309—Chen et al.
U.S. Pat. No. 4,702,916—Geria, N.
U.S. Pat. No. 4,738,956—Scott et al.

What is claimed is:

1. A stick formulation comprising from about 30 to about 70% w/w wax, from about 10 to about 55% w/w oil, from about 1 to about 30% w/w water, a surfactant and lidocaine hydrochloride, wherein the lidocaine hydrochloride is a least partially dissolved in water droplets dispersed in the wax.

2. The stick formulation of claim 1 further defined as comprising about 15 to about 40% w/w oil.

3. The stick formulation of claim 1, further defined as comprising about 40% to about 50% w/w wax.

4. The stick formulation of claim 1, further defined as comprising about 3 to 6% w/w water.

5. The stick formulation of claim 1, further defined as comprising about 15% to about 40% w/w of oil.

6. The stick formulation of claim 1, wherein the surfactant is a water in oil surfactant.

7. The stick formulation of claim 6 further defined as comprising about 0.2 to about 20% w/w of the surfactant.

8. The stick formulation of claim 7 further defined as comprising about 2.5 to about 5% w/w of the surfactant.

9. The stick formulation of claim 6 wherein the surfactant is propoxylated myristyl alcohol.

10. The stick formulation of claim 1 wherein said wax is beeswax, ceresin, cetyl alcohol, WITEPSOL® W35 or a combination of these.

11. The stick formulation of claim 1, wherein said oil is sesame oil, mineral oil, castor oil, isopropyl myristate or a combination of these.

12. The stick formulation of claim 1, wherein said surfactant is further described as having a hydrophobic lipophilic balance of not greater than 9.

13. The stick formulation of claim 1 wherein said surfactant is propoxylated myristyl alcohol, sorbitan trioleate, sorbitan tristearate, sorbitan sesquioleate, sorbitan monoleate, sorbitan monostearate, sorbitan monopalmitate, sorbitan monolaurate, glyceryl monostearate or a combination of these.

14. The stick formulation of claim 1 further comprising a semi-solid vehicle with a melting point between about 38° C. and about 60° C.

15. The stick formulation of claim 14, wherein said semi-solid vehicle is cocoa butter, white petrolatum, hard fat with a hyroxyl value 40–50 or a combination of these.

16. The stick formulation of claim 1 further defined as comprising:

about 30 to 46% w/w wax;

about 12 to 20% w/w oil;

about 6 to 10% w/w surfactant;

about 18 to 25% w/w semi-solid vehicle;

about 1 to 4% w/w bioadhesive oil soluble polymer;

about 2 to 6% w/w water;

about 0.025 to 4% w/w lidocaine hydrochloride; and about 0.02 to 0.04% organic anti-oxidant.

17. The stick formation of claim 1 further defined as comprising:

about 17.4% w/w beeswax;

about 12% w/w hard fat with hydroxyl value of 40–50;

about 16% w/w ceresin;

about 9% w/w white petrolatum;

about 7.6% w/w cetyl alcohol;

about 9% w/w sesame oil;

about 7.19% w/w mineral oil;

about 5.5% w/w isopropyl myristate;

about 8% w/w propoxylated myristyl alcohol;

about 2% w/w polyvinylpyrrolidone/eicosene copolymer;

about 4% w/w water;

about 2% w/w lidocaine hydrochloride;

about 0.05% w/w $Na_2EDTA$;

about 0.02% w/w BHA;

about 0.02% w/w BHT;

about 0.2% w/w methyl paraben; and about 0.02% w/w propyl paraben.

* * * * *

UNITED STATES PATENT AND TRADEMARK OFFICE
CERTIFICATE OF CORRECTION

PATENT NO. : 5,622,993

DATED : April 22, 1997

INVENTOR(S) : James W. McGinity, et al.

It is certified that error appears in the above-indentified patent and that said Letters Patent is hereby corrected as shown below:

In claim 10, column 19, line 12, delete "WITEPSOL® W35" and insert --hard fat with a hydroxyl value of 40-50--, therefor.

Signed and Sealed this

Ninth Day of September, 1997

Attest:

BRUCE LEHMAN

*Attesting Officer*  *Commissioner of Patents and Trademarks*